US012745964B2

(12) United States Patent
Lee et al.

(10) Patent No.: US 12,745,964 B2
(45) Date of Patent: Sep. 29, 2026

(54) METHOD FOR CONTACT VERIFICATION BASED ON RECEIVED SIGNAL SIMILARITY AND APPARATUS THEREOF

(71) Applicant: KOREA INSTITUTE OF SCIENCE AND TECHNOLOGY, Seoul (KR)

(72) Inventors: Taikjin Lee, Seoul (KR); Hankyeol Kyung, Seoul (KR); Chansoo Kim, Seoul (KR); Sangkyung Kim, Seoul (KR); Beomju Shin, Seoul (KR); Taehun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 363 days.

(21) Appl. No.: 18/538,021

(22) Filed: Dec. 13, 2023

(65) Prior Publication Data

US 2025/0025107 A1 Jan. 23, 2025

(30) Foreign Application Priority Data

Jul. 18, 2023 (KR) ........................ 10-2023-0092832

(51) Int. Cl.
*A61B 5/00* (2006.01)
*G16H 80/00* (2018.01)

(52) U.S. Cl.
CPC .......... *A61B 5/7221* (2013.01); *A61B 5/7282* (2013.01); *G16H 80/00* (2018.01)

(58) Field of Classification Search
CPC .... A61B 5/7221; A61B 5/7282; G16B 20/00; G16B 30/10; G16B 40/00; G16B 5/00; G16H 80/00
See application file for complete search history.

(56) References Cited

U.S. PATENT DOCUMENTS

| | | | | |
|---|---|---|---|---|
| 2020/0411133 A1* | 12/2020 | Xu | | G16H 50/80 |
| 2022/0022821 A1* | 1/2022 | Rodgers | | A61B 5/746 |
| 2024/0395419 A1* | 11/2024 | Jain | | G16H 80/00 |

FOREIGN PATENT DOCUMENTS

| | | | |
|---|---|---|---|
| KR | 10-2021-0155563 A | 12/2021 |
| KR | 10-2356357 B1 | 2/2022 |
| KR | 10-2022-0074495 A | 6/2022 |

OTHER PUBLICATIONS

Korean Office Action Issued on Jul. 18, 2025, in Counterpart Korean Patent Application No. 10-2023-0092832 (6 Pages in English, 6 Pages in Korean).

* cited by examiner

*Primary Examiner* — Timothy X Pham
(74) *Attorney, Agent, or Firm* — NSIP Law

(57) ABSTRACT

The present disclosure relates to a contact verification technology based on signal similarity, and an apparatus of contact verification receives and stores spatiotemporal signal information capable of specifying time and space from a plurality of user equipments (UEs), extract the spatiotemporal signal information of a specific user among the stored spatiotemporal signal information, configure the extracted spatiotemporal signal information of the specific user as reference spatiotemporal signal information, and compare similarity between the reference spatiotemporal signal information and the other stored spatiotemporal signal information, and determine whether or not there is contact between the specific user and another user based on the similarity.

15 Claims, 5 Drawing Sheets

(A)

(B)

(C)

METHOD FOR CONTACT VERIFICATION BASED ON RECEIVED SIGNAL SIMILARITY AND APPARATUS THEREOF

CROSS-REFERENCE TO RELATED APPLICATION

The present application claims the benefit of an earlier filing date and right of priority to Application No. KR 10-2023-0092832 filed on 18 Jul. 2023 in Korea, the contents of which are hereby incorporated by reference in its entirety.

BACKGROUND OF THE INVENTION

Field of the Invention

The present disclosure relates to technology for preventing infectious diseases and the spread of the infectious diseases, and relates to a method for determining whether there is contact between user equipment (UE) users based on similarity of signals received from the user equipment (UE) and an apparatus thereof.

Description of the Related Art

Recently, with the development of transportation methods and the increase in trade between countries, the need for a national infectious disease management model is emerging due to the frequent occurrence of new infectious diseases transmitted through human-to-human contact.

In particular, coronavirus-19 (COVID-19) is a highly contagious respiratory disease caused by a new type of coronavirus (SARS-CoV-2) that has spread throughout China and the world since it first occurred in Wuhan, China, as it is spread through droplets produced when coughing or sneezing, it is very important to identify the movement routes of confirmed patients and block further transmission.

Currently, a method of manually writing a guest book is being used or creating an electronic access register using QR codes is being used to track and manage infectious disease patients. However, this conventional method is not effective enough in an environment where specific personnel reside and move frequently. For example, medical and nursing institutions, public institutions, and other facilities use wireless signals to measure the movement routes of specific individuals in real time or at short time intervals when necessary, and collect and store them in a database. Contacts can be determined by comparing each individual's movement routes by time stored in the database, but since the search volume increases in proportion to the number of registered people and time, there is a problem that efficiency is greatly reduced when processing big data. Additionally, a huge amount of data places a large load on the system, making it difficult to expect fast processing results and accuracy.

In addition, there are various prior technologies that disclose individual movement route tracking technology based on conventional location information, but in identifying the movement routes of individuals who have been in contact with infectious disease patients during the outbreak of an infectious disease, as problems arise with the use of personal information called location information, improvement measures are needed.

SUMMARY OF THE INVENTION

The technical problem to be solved by the embodiments of the present disclosure aims to overcome problems related to personal information generated through the use of personal location information in verifying personal contact with a patient with an infectious disease. In addition, the purpose is to increase the accuracy of contact judgment by processing only data from various wireless signals such as WiFi, Bluetooth, LTE, and 5G received from the user's device, and to contribute to preventing the spread of infectious diseases and preventing it in advance by increasing the efficiency of data processing and making it easier to extract contact information.

In order to solve the above technical problem, a method for contact verification based on signal similarity according to an embodiment of the present disclosure comprises receiving and storing spatiotemporal signal information capable of specifying time and space from a plurality of user equipments (UEs) by an apparatus of contact verification; extracting spatiotemporal signal information of a specific user among the stored spatiotemporal signal information by the apparatus of contact verification; configuring the extracted spatiotemporal signal information of the specific user as reference spatiotemporal signal information, and comparing similarity between the reference spatiotemporal signal information and the other stored spatiotemporal signal information by the apparatus of contact verification; and determining whether or not there is contact between the specific user and another user based on the similarity by the apparatus of contact verification.

In a method for contact verification according to one embodiment, the spatiotemporal signal information may be temporal and spatial fingerprints (TSF) that is continuously measured over a certain period of time from at least one sensor in the user equipment (UE), and indicates space state information over time, and the TSF may include a signal type of the spatiotemporal signal information measured through the user equipment (UE), signal strength according to the signal type, and a timestamp indicating information about a time at which the signal type and the signal strength were measured.

In a method for contact verification according to one embodiment, the TSF may further include a state value of an environment indicating changes in the environment, and the state value of the environment may be at least one or a combination of a characteristic value of atmospheric pressure according to changes in atmospheric pressure in a space where the user stayed, a characteristic value of sound according to changes in sound in the space, and a characteristic value of temperature according to temperature changes in the space.

In a method for contact verification according to one embodiment, the receiving and storing spatiotemporal signal information may be matching a user equipment (UE) identifier with the spatiotemporal signal information and storing it.

In a method for contact verification according to one embodiment, the extracting spatiotemporal signal information of a specific user may be selecting spatiotemporal signal information corresponding to the spatiotemporal signal information of the specific user from a plurality of stored spatiotemporal signal information when the specific user is determined to be infected.

In a method for contact verification according to one embodiment, the comparing similarity may include performing a first similarity test to search spatiotemporal signal information having timestamp information similar to timestamp information of the reference spatiotemporal signal information among a plurality of stored spatiotemporal signal information; performing a second similarity test to search spatiotemporal signal information having a signal type and signal strength similar to a signal type and signal strength of the reference spatiotemporal signal information among the spatiotemporal signal information searched as a result of the first similarity test; and performing a third similarity test to search spatiotemporal signal information having a state value of an environment similar to a state value of an environment of the reference spatiotemporal signal information, when it contains environmental state values indicating changes in the environment, among the spatiotemporal signal information searched as a result of the second similarity test.

In a method for contact verification according to one embodiment, the determining whether or not there is contact may be verifying a user equipment (UE) identifier that measured spatiotemporal signal information similar to the reference spatiotemporal signal information of the specific user, and classifying the user as a contact or non-contact.

Furthermore, the following provides a computer-readable recording medium that records a program for executing the method for contact verification described above on a computer.

In order to solve the above technical problem, an apparatus of contact verification based on signal similarity according to an embodiment of the present disclosure comprises a communication module configured to receive spatiotemporal signal information from a plurality of user equipments (UEs); and a processor configured to store the spatiotemporal signal information, extract the spatiotemporal signal information of a specific user among the stored spatiotemporal signal information, configure the extracted spatiotemporal signal information of the specific user as reference spatiotemporal signal information, and compare similarity between the reference spatiotemporal signal information and the other stored spatiotemporal signal information, and determine whether or not there is contact between the specific user and another user based on the similarity.

In an apparatus of contact verification according to one embodiment, the processor may match a user equipment (UE) identifier with the spatiotemporal signal information and store it, the spatiotemporal signal information may be temporal and spatial fingerprints (TSF) that is continuously measured over a certain period of time from at least one sensor in the user equipment (UE), and indicates space state information over time, and the TSF may include a signal type of the spatiotemporal signal information measured through the user equipment (UE), signal strength according to the signal type, and a timestamp indicating information about a time at which the signal type and the signal strength were measured.

In an apparatus of contact verification according to one embodiment, the processor may select spatiotemporal signal information corresponding to the spatiotemporal signal information of the specific user from a plurality of stored spatiotemporal signal information when the specific user is determined to be infected.

In an apparatus of contact verification according to one embodiment, the processor may perform a first similarity test to search spatiotemporal signal information having timestamp information similar to timestamp information of the reference spatiotemporal signal information among a plurality of stored spatiotemporal signal information, perform a second similarity test to search spatiotemporal signal information having a signal type and signal strength similar to a signal type and signal strength of the reference spatiotemporal signal information among the spatiotemporal signal information searched as a result of the first similarity test, and perform a third similarity test to search spatiotemporal signal information having a state value of an environment similar to a state value of an environment of the reference spatiotemporal signal information, when it contains environmental status values that indicate changes in the environment, among the spatiotemporal signal information searched as a result of the second similarity test.

In an apparatus of contact verification according to one embodiment, the processor may verify a user equipment (UE) identifier that measured spatiotemporal signal information similar to the reference spatiotemporal signal information of the specific user, and classify the user as a contact or non-contact.

In an apparatus of contact verification according to one embodiment, the processor may transmit an infectious disease testing recommendation message to infected people depending on whether or not there is the determined contact.

According to the embodiments of the present disclosure described above, a technology for identifying the user's movement routes was proposed by comparing the similarity between signals received from the user equipment (UE). The proposed technology does not use the user's location information at all because it only compares the similarity of the signals themselves. As a result, it is free from privacy infringement issues that arise when determining whether or not there is contact between a user and an infectious disease patient. In addition, it is economical because there is no need to use resources to calculate location information, and it is easy to extract contact information, enabling rapid response to the spread of infectious diseases.

DETAILED DESCRIPTION OF THE EMBODIMENTS

Figure 1:
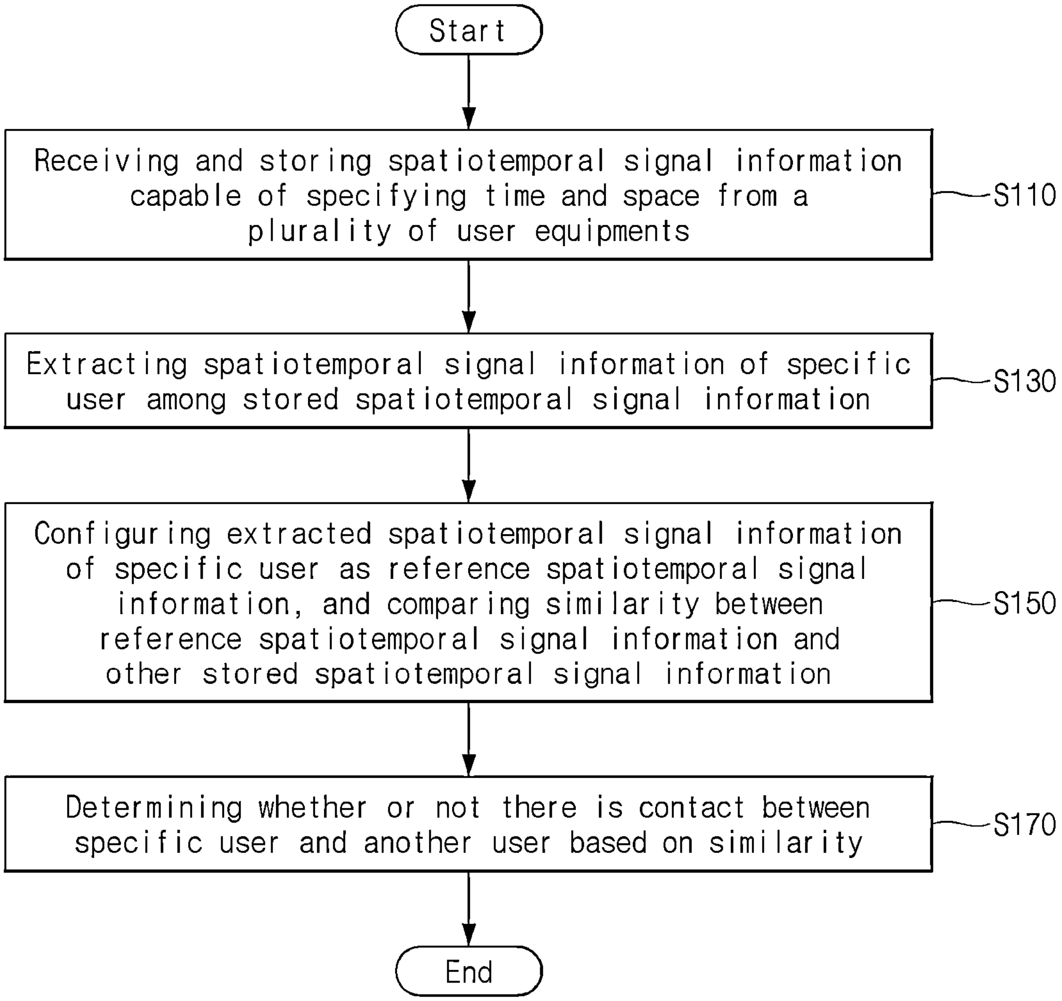
FIG. 1 is a flowchart illustrating a method for contact verification based on signal similarity according to an embodiment.

Before describing embodiments of the present disclosure in detail, it is introduced that the goals that appear in the field of technology for preventing contagious diseases or infectious diseases and preventing the spread of contagious diseases or infectious diseases in which the embodiments of the present disclosure are implemented and the technical means and configurations that can be considered to solve these goals.

Since coronavirus-19 (COVID-19) broke out in December 2019 and spread around the world, many studies have been conducted to prevent and prevent in advance the spread of infectious diseases. Typically, there are many technologies and studies that track the movement routes and contacts of infected people with infectious diseases. For example, obtaining personal ID (identifier) information of a personal user equipment (UE) carried by an individual using a plurality of identification information scanners installed in a plurality of places, respectively, and storing the time information and location information at which positioning of the personal ID information is made, through this, there is technology to trace infected people and their contacts. In addition, it has emerged the technology for collecting information on all close contacts at risk of infection within a specific facility by building an Internet of Things (IoT)-based sensor network within a specific facility, and tracking even the possibility of infection by deploying fixed Internet of Things sensors in areas at risk of infection in addition to mobile Internet of Things sensors.

However, all of the above-described technologies continuously store data estimating the locations of all personnel, so complex calculations are required and high costs may occur. In addition, if an infected person occurs later, a problem arises in using location information in determining whether or not there has been contact with personnel whose movement routes overlap with the infected person. User location information is a very important personal information issue, according to the Location Information Act, it is divided into "location information" and "personal location information" and their legal treatment is different, since the concept of "location information" is also defined very comprehensively, ultimately, using location information can cause various problems because it is information that is more closely related to an individual's human rights than to individual identification.

The contact verification technology based on signal similarity described in the present disclosure does not use any information and data related to location in determining whether an individual has been in contact with an infected person carrying an infectious disease. Therefore, the contact verification technology is relatively free from privacy issues compared to the technologies described above, and has the advantage of being able to be implemented at low cost by comparing signal similarity and testing only when an infected person is identified.

Hereinafter, embodiments of the present disclosure will be described in detail with reference to the drawings. However, detailed descriptions of known functions or configurations that may obscure the gist of the embodiments are omitted in the following description and attached drawings. In addition, throughout the specification, 'including' a certain component does not mean excluding other components unless specifically stated to the contrary, but rather means that other components may be further included.

Additionally, terms such as first, second, etc. may be used to describe various components, but the components should not be limited by the above terms. The above terms may be used for the purpose of distinguishing one component from another component. For example, a first component may be referred to as a second component without departing from the scope of the present disclosure, and similarly, the second component may also be referred to as the first component.

The terms used in the present disclosure are only used to describe specific embodiments and are not intended to limit the present disclosure. Singular expressions include plural expressions unless the context clearly indicates otherwise. In the present disclosure, terms such as "comprise" or "include" are intended to designate the presence of described features, numbers, steps, operations, components, parts, or combinations thereof, and it should be understood that this does not exclude in advance the presence or addition of one or more other features, numbers, steps, operations, components, parts, or combinations thereof.

Unless specifically defined otherwise, all terms used herein, including technical or scientific terms, have the same meaning as generally understood by a person of ordinary skill in the technical field to which the present disclosure pertains. Terms such as those defined in commonly used dictionaries should be interpreted as having a meaning consistent with the meaning in the context of the related technology, and unless clearly defined in the present disclosure, should not be interpreted in an idealized or excessively formal meaning.

FIG. 1 is a flowchart illustrating a method for contact verification based on signal similarity according to an embodiment.

In step S110, an apparatus of contact verification receives and stores spatiotemporal signal information capable of specifying time and space from a plurality of user equipments (UEs). In this process, it may match and store a user equipment (UE) identifier with the spatiotemporal signal information. At this time, the user equipment (UE) is not limited to the user's mobile communication user equipment (UE) but may include the user's wearable device capable of wireless communication.

In step S130, the apparatus of contact verification extracts the spatiotemporal signal information of a specific user among the stored spatiotemporal signal information. In this process, when the specific user is determined to be infected, it may select spatiotemporal signal information corresponding to the spatiotemporal signal information of the specific user from a plurality of stored spatiotemporal signal information In step S150, the apparatus of contact verification configures the extracted spatiotemporal signal information of the specific user as reference spatiotemporal signal information, and compares similarity between the reference spatiotemporal signal information and the other stored spatiotemporal signal information. In this process, it may perform a first similarity test to search spatiotemporal signal information having timestamp information similar to timestamp information of the reference spatiotemporal signal information among a plurality of stored spatiotemporal signal information, perform a second similarity test to search spatiotemporal signal information having a signal type and signal strength similar to a signal type and signal strength of the reference spatiotemporal signal information among the spatiotemporal signal information searched as a result of the first similarity test, and perform a third similarity test to search spatiotemporal signal information having a state value of an environment similar to a state value of an environment of the reference spatiotemporal signal information, when it contains environmental status values that indicate changes in the environment, among the spatiotemporal signal information searched as a result of the second similarity test. At this time, the similarity can be interpreted as correlation, and in the method of comparing the similarity, likelihood can be used as the correlation coefficient, which is an indicator of how a change in one of two variables occurs in response to a change in the other variable, and a measure that can evaluate several possible hypotheses based on the results shown.

In step S170, the apparatus of contact verification determine whether or not there is contact between the specific user and another user based on the similarity. In this process, it may verify a user equipment (UE) identifier that measured spatiotemporal signal information similar to the reference spatiotemporal signal information of the specific user, and classify the user as a contact or non-contact.

The spatiotemporal signal information will be described in detail below with reference to FIGS. 2 and 3.

Figure 2:
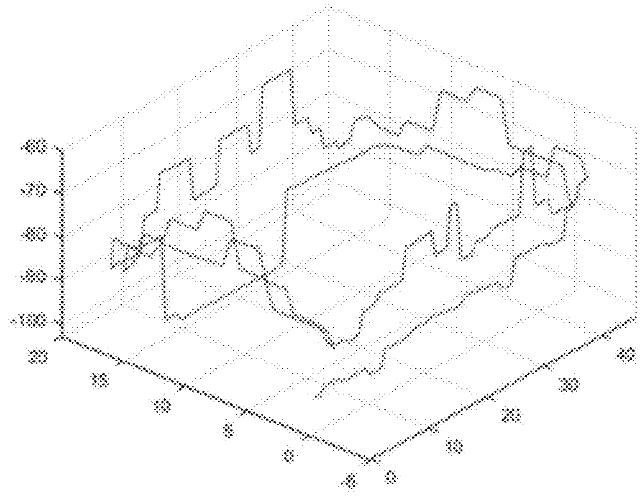
FIG. 2 is a diagram illustrating different signal patterns received by a user equipment (UE) depending on space.
Figure 2:
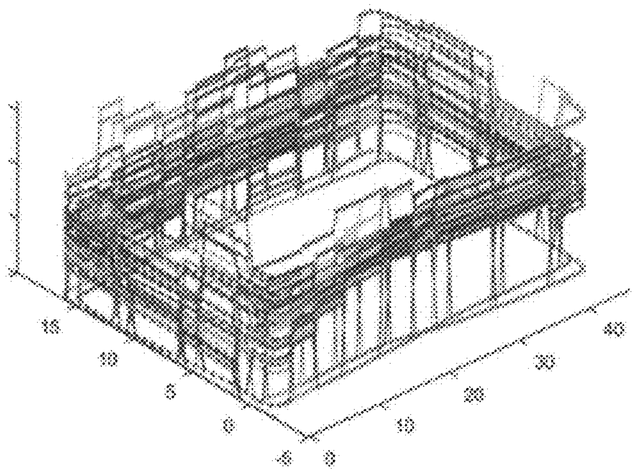
Figure 2:
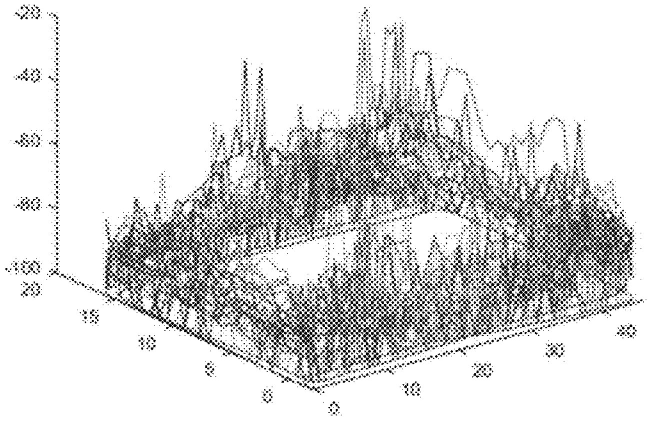

FIG. 2 is a diagram illustrating different signal patterns received by a user equipment (UE) depending on space.

FIG. 2(A) shows a long term evolution (LTE) signal pattern, which is one of wireless communication types, (B) shows WiFi signal patterns, and (C) shows Bluetooth signal patterns. The signal pattern can be interpreted as signal strength. The signals (A), (B), and (C) represent only signal patterns extracted from representative patterns of the signal patterns received every 30 seconds and stored in the server in configuring the measurement interval as 30 seconds while being received by the server. Through this, the cost used for signal processing and storage can be reduced by storing part of the signal rather than storing the received signal information itself.

Regarding (A) of FIG. 2, when the spatiotemporal signal information is a wireless communication signal, in the process of receiving and storing the spatiotemporal signal information, which is step S110 of FIG. 1, it can be stored including the type of carrier and communication standard of the wireless communication signal. In addition, in the process of comparing the similarity between the spatiotemporal signal information, which is step S150 of FIG. 1, similarity between wireless communication signals of each of the reference spatiotemporal signal information and the other stored spatiotemporal signal information may be compared targeting spatiotemporal signal information matching at least one or a combination of the type of carrier and the communications standard.

Regarding (B) of FIG. 2, when the spatiotemporal signal information is WiFi, in the process of the receiving and storing spatiotemporal signal information, which is step S110 of FIG. 1, an access point (AP) identifier, frequency, and channel of the WiFi, may be included and stored. In addition, in the process of the comparing similarity between the spatiotemporal signal information, which is step S150, similarity between WiFi signals of each of the reference spatiotemporal signal information and the other stored spatiotemporal signal information may be compared targeting spatiotemporal signal information matching at least one or a combination of the access point (AP) identifier, frequency, and channel of the WiFi.

Regarding (C) of FIG. 2, when the spatiotemporal signal information is Bluetooth, in the process of the receiving and storing spatiotemporal signal information, which is step S110 of FIG. 1, a Bluetooth identifier may be included and stored. In addition, in the process of the comparing similarity between the spatiotemporal signal information, which is step S150, similarity between Bluetooth signals of each of the reference spatiotemporal signal information and the other stored spatiotemporal signal information may be compared targeting spatiotemporal signal information matching the Bluetooth identifier.

Depending on the type of the spatiotemporal signal information described above, it can be easy to specify spatiotemporal signal information by varying the storage items in consideration of the characteristics of each signal information. In addition, as the storage items vary depending on the type of the spatiotemporal signal information, there is no need to fully scan all data in the table where the spatiotemporal signal information is stored, and it is possible to quickly determine whether users have been in contact with an infected person.

Figure 3:
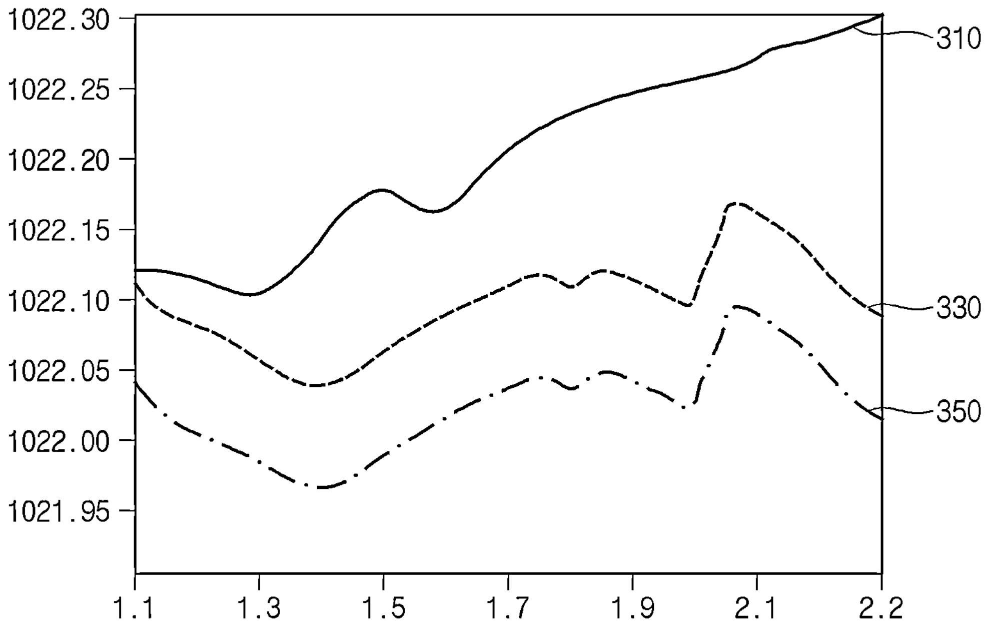
FIG. 3 is a diagram illustrating a change in atmospheric pressure measured through an atmospheric pressure sensor in a user equipment (UE) depending on space.

FIG. 3 is a diagram illustrating over time a measure of change in atmospheric pressure measured through an atmospheric pressure sensor in a user equipment (UE) depending on space.

The measurement value of the change in the atmospheric pressure is one of state values of space and can be measured through an atmospheric pressure sensor built into the user equipment (UE). At this time, the atmospheric pressure sensor may be at least one of a GPS altimeter, a location-based altimeter, and an atmospheric pressure altimeter, or a combination thereof. There are various factors that can change the atmospheric pressure in space. For example, factors may be whether a heater is running, how hard a door is opened when an individual enters or exits the room, and whether there is ventilation, but are not limited to this, and may include various variable factors that can be measured while changing atmospheric pressure.

Based on this, as shown in FIG. 3, it can be seen that the measured change values of atmospheric pressure, 310, 330, and 350, measured by the user equipment (UE) are shown in a graph. The user equipment (UE) that measured 310 was in a different space from the user equipment (UE) that measured 330 and 350, and in fact it can be seen that the pattern of change in the measured value of 310 is different from that of the measured value of 330 and 350. Additionally, it can be seen that the shape of the graph of the change in measured values of 330 and 350 is the same. In other words, it can be seen that the user equipment (UE) that measured 330 and the user equipment (UE) that measured 350 are in the same space.

Moreover, as the measured values of 330 and 350 are close, it is also possible to estimate how close the user equipments (UEs) are to each other within the same space. For example, if the user equipment (UE) that measured 330 is the user equipment (UE) of an infected person, as the measured value of 350 is to the measured value of 330, since there is a very high possibility that they came into contact with each other, the user of the user equipment (UE) that measured 350 can be classified as a close contact. Conversely, as it moves away from the measured value of 330, the user of the user equipment (UE) that measured 350 can be classified as simple contacts or non-contacts.

FIG. 3 shows an example of measured values according to changes in atmospheric pressure in space, but as one of the state values of the space, a measurement value based on a change in the sound of the space or a measurement value based on a change in the temperature of the space can be used to determine whether or not there is contact with an infected person. At this time, the sensor that measures the change in sound in the space may be a sound sensor built into the user equipment (UE), and the sensor that measures the change in temperature in the space may be a temperature sensor built in the user equipment (UE).

Through the description of FIGS. 2 and 3 described above, the spatiotemporal signal information may be temporal and spatial fingerprints (TSF) that is continuously measured over a certain period of time from at least one sensor in the user equipment (UE), and indicates space state information over time, and the TSF may include a signal type of the spatiotemporal signal information measured through the user equipment (UE), signal strength according to the signal type, and a timestamp indicating information about a time at which the signal type and the signal strength were measured, and may further include a state value of an environment indicating changes in the environment, and the state value of the environment may be at least one or a combination of a characteristic value of atmospheric pressure according to changes in atmospheric pressure in a space where the user stayed, a characteristic value of sound according to changes in sound in the space, and a characteristic value of temperature according to temperature changes in the space.

Figure 4:
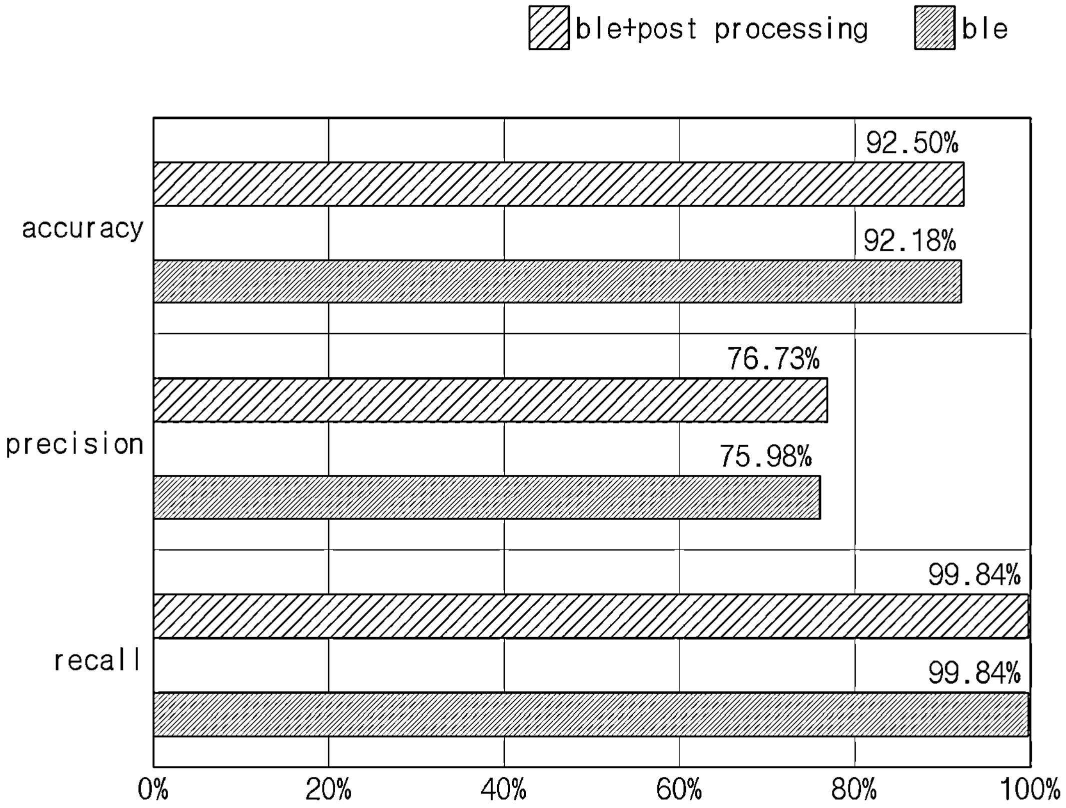
FIG. 4 is a diagram comparing performance of an apparatus of contact verification with or without post processing through a multi-layer perceptron (MLP) model.

FIG. 4 is a diagram comparing performance of an apparatus of contact verification with or without post processing through a multi-layer perceptron (MLP) model.

Figure 5:
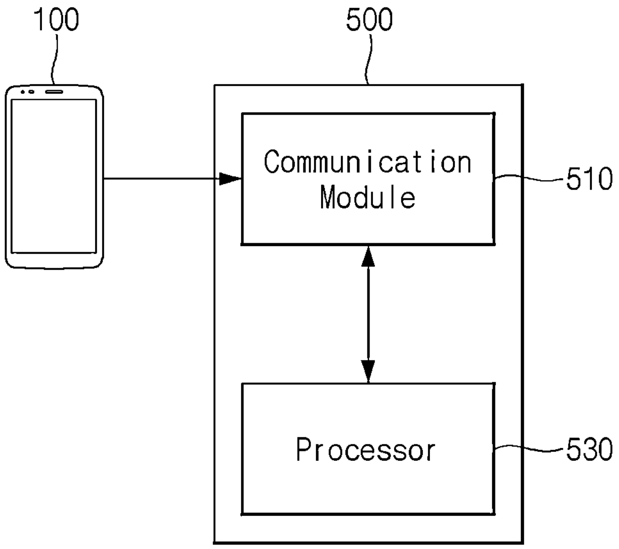
FIG. 5 is a block diagram illustrating an apparatus that performs contact verification based on signal similarity according to an embodiment.

The Accuracy item in FIG. 4 indicates the probability of accurately finding an actual contact as a contact in the sample, and the probability of accurately finding a non-contact as a non-contact. The Precision item indicates the probability of actually being a contact among those found as contacts in the sample. The recall item indicates the probability of finding an actual contact. The key to finding contacts in this field of technology is not to miss contacts, so it is important to design the apparatus with the goal of maximizing the above recall items. As a result of the actual experiment, as shown in FIG. 5, the recall, which is the probability of finding an actual contact as a contact, is estimated to be 99.8%. In other words, virtually all contacts can be found. In addition, because only signal characteristics are compared, in fact, the contact person's movement routes can be identified in about 10 minutes. In this process, it was verified that no location information is used at al, and it is free from personal information issues because the location of contact is not specifically known, and there are few issues with innocent victims resulting from the provision of contact information.

FIG. 5 is a block diagram illustrating an apparatus for generating multiple questions according to an embodiment, and a reconstruction of a method for contact verification based on signal similarity according to the embodiment of FIG. 1 from a perspective of hardware configuration.

An apparatus of contact verification 500 may include a communication module 510 and a processor 530.

The communication module 510 receives spatiotemporal signal information from a plurality of user equipments (UEs) 100.

The processor 530 stores the spatiotemporal signal information, extract the spatiotemporal signal information of a specific user among the stored spatiotemporal signal information, configure the extracted spatiotemporal signal information of the specific user as reference spatiotemporal signal information, and compare similarity between the reference spatiotemporal signal information and the other stored spatiotemporal signal information, and determine whether or not there is contact between the specific user and another user based on the similarity.

The processor 530 may match a user equipment (UE) identifier with the spatiotemporal signal information and store it, the spatiotemporal signal information may be temporal and spatial fingerprints (TSF) that is continuously measured over a certain period of time from at least one sensor in the user equipment (UE) 100, and indicates space state information over time, and the TSF may include a signal type of the spatiotemporal signal information measured through the user equipment (UE) 100, signal strength according to the signal type, and a timestamp indicating information about a time at which the signal type and the signal strength were measured.

The processor 530 may select spatiotemporal signal information corresponding to the spatiotemporal signal information of the specific user from a plurality of stored spatiotemporal signal information when the specific user is determined to be infected.

The processor 530 may perform a first similarity test to search spatiotemporal signal information having timestamp information similar to timestamp information of the reference spatiotemporal signal information among a plurality of stored spatiotemporal signal information, perform a second similarity test to search spatiotemporal signal information having a signal type and signal strength similar to a signal type and signal strength of the reference spatiotemporal signal information among the spatiotemporal signal information searched as a result of the first similarity test, and perform a third similarity test to search spatiotemporal signal information having a state value of an environment similar to a state value of an environment of the reference spatiotemporal signal information, when it contains environmental status values that indicate changes in the environment, among the spatiotemporal signal information searched as a result of the second similarity test.

The processor 530 may verify a user equipment (UE) identifier that measured spatiotemporal signal information similar to the reference spatiotemporal signal information of the specific user, and classify the user as a contact or non-contact.

The processor 530 may transmit an infectious disease testing recommendation message to infected people depending on whether or not there is the determined contact.

According to the above-described embodiments of the present disclosure, a technology for identifying the user's movement routes by comparing the similarity between signals received from the user equipment (UE) has been proposed. The proposed technology does not use the user's location information at all because it only compares the similarity of the signals themselves. As a result, it is free from privacy infringement issues that arise when determining whether or not there is contact between a user and an infectious disease patient. In addition, it is economical because there is no need to use resources to calculate location information, and it is easy to extract contact information, enabling rapid response to the spread of infectious diseases.

The embodiments of the present disclosure may be achieved by various means, for example, hardware, firmware, software, or a combination thereof. In a hardware configuration, the methods according to the embodiments of the present disclosure may be achieved by one or more Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, microcontrollers, microprocessors, etc. In a firmware or software configuration, the embodiments of the present disclosure may be implemented in the form of a module, a procedure, a function, etc. For example, software code may be stored in a memory unit and executed by a processor. The memories may be located at the interior or exterior of the processors and may transmit data to and receive data from the processors via various known means.

On the other hand, embodiments of the present disclosure may be implemented as computer readable codes on a computer-readable recording medium. The computer-readable recording medium includes all types of recording devices in which data that can be read by a computer system is stored. Examples of computer-readable recording media include ROM, RAM, CD-ROM, magnetic tape, floppy disk, optical data storage device, etc. In addition, the computer-readable recording medium may be distributed to computer systems connected through a network, so that computer-readable codes may be stored and executed in a distributed manner. In addition, functional programs, codes, and code segments for implementing the embodiments can be easily inferred by programmers in the technical field to which the present disclosure belongs.

In the above, the present disclosure has been examined focusing on its various embodiments. Those skilled in the art of the present disclosure will understand that various embodiments may be implemented in modified forms without departing from the essential characteristics of the present disclosure. Therefore, the disclosed embodiments should be considered from an illustrative rather than a restrictive perspective. The scope of the present disclosure is indicated in the claims rather than the foregoing description, and all differences within the equivalent scope should be construed as being included in the present disclosure.

What is claimed is:

1. A method for contact verification comprising:

receiving and storing spatiotemporal signal information capable of specifying time and space from a plurality of user equipments (UEs) by an apparatus of contact verification;

extracting spatiotemporal signal information of a specific user among the stored spatiotemporal signal information by the apparatus of contact verification;

configuring the extracted spatiotemporal signal information of the specific user as reference spatiotemporal signal information, and comparing similarity between the reference spatiotemporal signal information and the other stored spatiotemporal signal information by the apparatus of contact verification; and determining whether or not there is contact between the specific user and another user based on the similarity by the apparatus of contact verification, wherein comparing the similarity comprises:

performing a first similarity test to search spatiotemporal signal information having timestamp information similar to timestamp information of the reference spatiotemporal signal information among a plurality of stored spatiotemporal signal information;

performing a second similarity test to search spatiotemporal signal information having a signal type and signal strength similar to a signal type and signal strength of the reference spatiotemporal signal information among the spatiotemporal signal information searched as a result of the first similarity test; and performing a third similarity test to search spatiotemporal signal information having a state value of an environment similar to a state value of an environment of the reference spatiotemporal signal information, when it contains environmental state values indicating changes in the environment, among the spatiotemporal signal information searched as a result of the second similarity test.

2. The method of claim 1, wherein the spatiotemporal signal information is temporal and spatial fingerprints (TSF) that is continuously measured over a certain period of time from at least one sensor in the user equipment (UE), and indicates space state information over time, and the TSF includes a signal type of the spatiotemporal signal information measured through the user equipment (UE), signal strength according to the signal type, and a timestamp indicating information about a time at which the signal type and the signal strength were measured.

3. The method of claim 2, wherein the TSF further includes a state value of an environment indicating changes in the environment, and the state value of the environment is at least one or a combination of a characteristic value of atmospheric pressure according to changes in atmospheric pressure in a space where the user stayed, a characteristic value of sound according to changes in sound in the space, and a characteristic value of temperature according to temperature changes in the space.

4. The method of claim 1, wherein the receiving and storing spatiotemporal signal information is matching a user equipment (UE) identifier with the spatiotemporal signal information and storing it.

5. The method of claim 1, wherein the extracting spatiotemporal signal information of a specific user is selecting spatiotemporal signal information corresponding to the spatiotemporal signal information of the specific user from a plurality of stored spatiotemporal signal information when the specific user is determined to be infected.

6. The method of claim 1, wherein the determining whether or not there is contact is verifying a user equipment (UE) identifier that measured spatiotemporal signal information similar to the reference spatiotemporal signal information of the specific user, and classifying the user as a contact or non-contact.

7. The method of claim 1, wherein, when the spatiotemporal signal information is a wireless communication signal, the receiving and storing spatiotemporal signal information is including and storing a type of carrier and communication standard of the wireless communication signal, and the comparing similarity between the spatiotemporal signal information is comparing similarity between wireless communication signals of each of the reference spatiotemporal signal information and the other stored spatiotemporal signal information targeting spatiotemporal signal information matching at least one or a combination of the type of carrier and the communications standard.

8. The method of claim 1, wherein when the spatiotemporal signal information is WiFi, the receiving and storing spatiotemporal signal information is including and storing an access point (AP) identifier, frequency, and channel of the WiFi, and the comparing similarity between the spatiotemporal signal information is comparing similarity between WiFi signals of each of the reference spatiotemporal signal information and the other stored spatiotemporal signal information targeting spatiotemporal signal information matching at least one or a combination of the access point (AP) identifier, frequency, and channel of the WiFi.

9. The method of claim 1, wherein when the spatiotemporal signal information is Bluetooth, the receiving and storing spatiotemporal signal information is including and storing a Bluetooth identifier, and the comparing similarity between the spatiotemporal signal information is comparing similarity between Bluetooth signals of each of the reference spatiotemporal signal information and the other stored spatiotemporal signal information targeting spatiotemporal signal information matching the Bluetooth identifier.

10. One or more non-transitory computer-readable medium storing one or more instructions, wherein the computer-readable medium is configured to:

receive and store spatiotemporal signal information capable of specifying time and space from a plurality of user equipments (UEs), extract the spatiotemporal signal information of a specific user among the stored spatiotemporal signal information, configure the extracted spatiotemporal signal information of the specific user as reference spatiotemporal signal information, and compare similarity between the reference spatiotemporal signal information and the other stored spatiotemporal signal information, and determine whether or not there is contact between the specific user and another user based on the similarity, wherein the computer-readable medium is configured to compare the similarity between the reference spatiotemporal signal information and the other stored spatiotemporal signal information by:

performing a first similarity test to search spatiotemporal signal information having timestamp information similar to timestamp information of the reference spatiotemporal signal information among a plurality of stored spatiotemporal signal information;

performing a second similarity test to search spatiotemporal signal information having a signal type and signal strength similar to a signal type and signal strength of the reference spatiotemporal signal information among the spatiotemporal signal information searched as a result of the first similarity test; and performing a third similarity test to search spatiotemporal signal information having a state value of an environment similar to a state value of an environment of the reference spatiotemporal signal information, when it contains environmental status values that indicate changes in the environment, among the spatiotemporal signal information searched as a result of the second similarity test.

11. An apparatus of contact verification comprising:

a communication module configured to receive spatiotemporal signal information from a plurality of user equipments (UEs); and a processor configured to store the spatiotemporal signal information, extract the spatiotemporal signal information of a specific user among the stored spatiotemporal signal information, configure the extracted spatiotemporal signal information of the specific user as reference spatiotemporal signal information, and compare similarity between the reference spatiotemporal signal information and the other stored spatiotemporal signal information, and determine whether or not there is contact between the specific user and another user based on the similarity, wherein the processor is configured to compare the similarity between the reference spatiotemporal signal information and the other stored spatiotemporal signal information by:

performing a first similarity test to search spatiotemporal signal information having timestamp information similar to timestamp information of the reference spatiotemporal signal information among a plurality of stored spatiotemporal signal information;

performing a second similarity test to search spatiotemporal signal information having a signal type and signal strength similar to a signal type and signal strength of the reference spatiotemporal signal information among the spatiotemporal signal information searched as a result of the first similarity test; and performing a third similarity test to search spatiotemporal signal information having a state value of an environment similar to a state value of an environment of the reference spatiotemporal signal information, when it contains environmental status values that indicate changes in the environment, among the spatiotemporal signal information searched as a result of the second similarity test.

12. The apparatus of claim 11, wherein the processor matches a user equipment (UE) identifier with the spatiotemporal signal information and stores it, the spatiotemporal signal information is temporal and spatial fingerprints (TSF) that is continuously measured over a certain period of time from at least one sensor in the user equipment (UE), and indicates space state information over time, and the TSF includes a signal type of the spatiotemporal signal information measured through the user equipment (UE), signal strength according to the signal type, and a timestamp indicating information about a time at which the signal type and the signal strength were measured.

13. The apparatus of claim 11, wherein the processor selects spatiotemporal signal information corresponding to the spatiotemporal signal information of the specific user from a plurality of stored spatiotemporal signal information when the specific user is determined to be infected.

14. The apparatus of claim 11, wherein the processor verifies a user equipment (UE) identifier that measured spatiotemporal signal information similar to the reference spatiotemporal signal information of the specific user, and classifies the user as a contact or non-contact.

15. The apparatus of claim 11, wherein the processor transmits an infectious disease testing recommendation message to infected people depending on whether or not there is the determined contact.

* * * * *